(12) United States Patent
Tong (10) Patent No.: US 12,383,238 B2
(45) Date of Patent: Aug. 12, 2025

(54) BLADDER VOLUME MEASURING METHOD AND SYSTEM (71) Applicants: Astrasono Technology Co., Ltd, Guangdong (CN); ASTRASONO MEDICAL INC, Kent, DE (US)

(72) Inventor: Weiqiang Tong, Guangdong (CN)

(73) Assignees: Astrasono Technology Co., Ltd, Shenzhen (CN); ASTRASONO MEDICAL INC, Dover, DE (US)

(*) Notice: Subject to any disclaimer, the term of this patent is extended or adjusted under 35 U.S.C. 154(b) by 0 days.

(21) Appl. No.: 18/423,510

(22) Filed: Jan. 26, 2024

(65) Prior Publication Data

US 2025/0152142 A1 May 15, 2025

(30) Foreign Application Priority Data

Nov. 13, 2023 (CN) .......................... 202311513480.7

(51) Int. Cl.
*A61B 8/00* (2006.01)
*A61B 8/08* (2006.01)
*G06T 7/00* (2017.01)
*G06T 7/11* (2017.01)
*G06T 7/62* (2017.01)
*G06T 7/70* (2017.01)

(52) U.S. Cl.
CPC ............ *A61B 8/5223* (2013.01); *A61B 8/085* (2013.01); *A61B 8/4466* (2013.01); *G06T 7/0012* (2013.01); *G06T 7/11* (2017.01); *G06T 7/62* (2017.01); *G06T 7/70* (2017.01); *G06T 2207/10132* (2013.01); *G06T 2207/30004* (2013.01)

(58) Field of Classification Search
CPC ..... A61B 8/5223; A61B 8/085; A61B 8/4466; G06T 7/0012; G06T 7/11; G06T 7/62; G06T 7/70; G06T 2207/10132; G06T 2207/30004
See application file for complete search history.

(56) References Cited

U.S. PATENT DOCUMENTS

2018/0330518 A1* 11/2018 Choi .................... A61B 8/5223
2021/0353261 A1* 11/2021 Ebata .................... A61B 8/085

* cited by examiner

*Primary Examiner* — Bo Joseph Peng
(74) *Attorney, Agent, or Firm* — Warner Norcross + Judd LLP (57) ABSTRACT

A bladder volume measuring method is disclosed. The measuring method is applied to a measuring device, the measuring device includes a detector for acquiring a sectional image of a bladder and rotatable around a first direction, and the first direction is a direction of a connecting line between the detector and a measured position. The measuring method includes: when the detector rotates around the first direction, acquiring a corresponding initial sectional image every time the detector rotates by a first preset angle; confirming a current position of the bladder according to all the initial sectional images, and generating and displaying corresponding prompt information; the prompt information being used for prompting a user to move the detector; and after the detector moves, when the detector rotates around the first direction again, acquiring a corresponding current sectional image at an interval of a second preset angle to calculate the bladder volume.

5 Claims, 9 Drawing Sheets

BLADDER VOLUME MEASURING METHOD AND SYSTEM

CROSS-REFERENCE TO RELATED APPLICATION

This application is based on and claims the benefit of priority from Chinese Patent Application No. 2023115134807, filed on 13 Nov. 2023, the entirety of which is incorporated by reference herein.

TECHNICAL FIELD

The present disclosure relates to the field of ultrasound imaging, and more particularly, to a bladder volume measuring method and system.

BACKGROUND

In the related art, urinary system examination typically involves measurement of a bladder volume through a bladder measuring instrument. The existing bladder volume measuring method often relies on a user to control a position and an angle of a detector through use experience and subjective feeling of the user to position a bladder of the subject. However, it is difficult to position the bladder directly and successfully only by the user to subjectively place a probe. In addition, the user cannot determine the next target moving direction of the probe, which leads to a long time required for positioning and reduces measurement efficiency.

SUMMARY

The present disclosure aims to solve at least one of the technical problems in the related art. Therefore, the present disclosure provides a bladder volume measuring method and system, which can prompt a user about a next moving direction of a detector.

According to a first aspect of the present disclosure, a bladder volume measuring method is provided, which is applied to a measuring device, wherein the measuring device comprises a detector for acquiring a sectional image of a bladder, the detector is capable of rotating around a first direction, and the first direction is a direction of a connecting line between the detector and a measured position; and the measuring method comprises:

when the detector rotates around the first direction, acquiring a corresponding initial sectional image every time the detector rotates by a first preset angle;

confirming a current position of the bladder according to all the initial sectional images, and generating and displaying corresponding prompt information; the prompt information being used for prompting a user to move the detector; and after the detector moves, when the detector rotates around the first direction again, acquiring a corresponding current sectional image at an interval of a second preset angle to calculate the bladder volume.

The bladder volume measuring method according to embodiments of the present disclosure at least has the following beneficial effects.

The measuring device disclosed in the embodiments of the present disclosure comprises the detector for acquiring the sectional image of the bladder, the detector is capable of rotating around the first direction, and the first direction is the direction of the connecting line between the detector and the measured position. The measuring method comprises the steps of, when the detector rotates around the first direction, acquiring the corresponding initial sectional image every time the detector rotates by the first preset angle; confirming the current position of the bladder according to all the initial sectional images, and generating and displaying the corresponding prompt information; the prompt information being used for prompting a user to move the detector; and after the detector moves, when the detector rotates around the first direction again, acquiring the corresponding current sectional image at the second preset angle to calculate the bladder volume. The present disclosure realizes that the user can accurately determine the current position of the bladder after placing the detector, and can send the prompt information to the user according to the current position of the bladder, so as to prompt the user about the next target moving direction of the detector, reduce the dependence on the use experience and subjective feeling of the user, improve the positioning accuracy of the bladder, greatly shorten the time required for positioning the bladder, improve the positioning efficiency of the bladder, further improve the bladder volume measurement accuracy and greatly improve the measurement efficiency at the same time. In addition, the full interaction between the measuring device and the user can also improve the use experience of the user.

According to some embodiments of the present disclosure, the confirming a current position of the bladder according to all the initial sectional images, and generating and displaying corresponding prompt information comprises:

confirming the initial sectional image with the largest bladder width according to all the initial sectional images;

after the detector rotates to an angle corresponding to the initial sectional image with the largest bladder width, acquiring a target sectional image; and acquiring orientation information of the bladder according to the target sectional image, and generating prompt information corresponding to the orientation information.

According to some embodiments of the present disclosure, the confirming the initial sectional image with the largest bladder width according to all the initial sectional images comprises:

acquiring initial edge data of the bladder in each initial sectional image;

calculating a bladder width corresponding to each initial sectional image according to each initial edge data; and comparing the bladder width corresponding to each initial sectional image to confirm the initial sectional image with the largest bladder width in all the initial sectional images.

According to some embodiments of the present disclosure, the orientation information comprises a target moving direction, and the acquiring orientation information of the bladder according to the target sectional image, and generating prompt information corresponding to the orientation information comprises:

dividing regions for the target section image to form two regions;

determining the target moving direction according to a region at which the bladder is located; and generating and displaying the prompt information corresponding to the target moving direction according to the target moving direction.

According to some embodiments of the present disclosure, the prompt information comprises a visual reference identifier, and the measuring device further comprises a display device for displaying the visual reference identifier, and the generating and displaying the prompt information corresponding to the target moving direction according to the target moving direction comprises:

generating and displaying the visual reference identifier; the visual reference identifier comprising a central point and a plurality of pointing identifier groups, the plurality of pointing identification groups being arranged around the central point at an interval of the first preset angle, and each pointing identifier group comprises a first identifier and a second identifier pointing to opposite directions, and the first identifier and the second identifier corresponding to the two regions one by one to represent the target moving direction; and highlighting the first identifier or the second identifier in the target identifier group.

According to some embodiments of the present disclosure, the measuring device further comprises a controller, a first driver for driving the detector to rotate around the first direction, and a second driver for driving the detector to swing around a second direction, the second direction is parallel to the measured position, the controller is connected with the first driver and the second driver to send an instruction signal, and the instruction signal comprises a first instruction and a second instruction; and the measuring method is applied to the controller, when the detector rotates around the first direction, the acquiring a corresponding initial sectional image every time the detector rotates by a first preset angle comprises:

sending the first instruction to the first driver; the first instruction being used for triggering the first driver to drive the detector to rotate around the first direction by the first preset angle;

sending the second instruction to the second driver to acquire the corresponding initial sectional image; the second instruction being used for triggering the second driver to drive the detector to swing around the second direction; and repeating the first operation and the second operation until the detector rotates by one circle.

According to some embodiments of the present disclosure, the acquiring a corresponding current sectional image at an interval of a second preset angle to calculate the bladder volume comprises:

acquiring all current edge data corresponding to all the current sectional images one by one according to all the current sectional images; and calculating the bladder volume according to all the current edge data.

According to some embodiments of the present disclosure, the acquiring a corresponding current sectional image at an interval of a second preset angle to calculate the bladder volume comprises:

acquiring all current edge data corresponding to all the current sectional images one by one according to all the current sectional images; and calculating the bladder volume according to all the current edge data.

According to a second aspect of the present disclosure, a bladder volume measuring system is provided, which is applied to a measuring device, wherein the measuring device comprises a detector for acquiring a sectional image of a bladder, the detector is capable of rotating around a first direction, and the first direction is a direction of a connecting line between the detector and a measured position; and the measuring system comprises:

an acquisition circuit configured for, when the detector rotates around the first direction, acquiring a corresponding initial sectional image every time the detector rotates by a first preset angle;

a generation circuit configured for confirming a current position of the bladder according to all the initial sectional images, and generating and displaying corresponding prompt information; the prompt information being used for prompting a user to move the detector; and a calculation circuit configured for, after the detector moves, when the detector rotates around the first direction again, acquiring a corresponding current sectional image at an interval of a second preset angle to calculate the bladder volume.

In a third aspect, the present disclosure provides an electronic device, comprising: a processor, a memory and a computer program stored on the memory and operatable on the processor, wherein the computer program, when executed by the processor, implements the steps of the bladder volume measuring method as described in the first aspect of the present disclosure above.

According to a fourth aspect of the present disclosure, a computer readable storage medium is provided, wherein: the computer readable storage medium stores a computer program thereon, and the computer program, when executed by a processor, implements the steps of the bladder volume measuring method as described in the first aspect of the present disclosure above.

Additional aspects and advantages of the present disclosure will be given in part in the following description, and will become apparent in part from the following description, or will be learned through the practice of the present disclosure.

BRIEF DESCRIPTION OF THE DRAWINGS

The present disclosure will be further explained with reference to the accompanying drawings and embodiments hereinafter, wherein.

REFERENCE NUMERALS 1000 refers to first direction; and 2000 refers to second direction;
400 refers to measuring system; 410 refers to acquisition circuit; 420 refers to generation circuit; and 430 refers to calculation circuit;
500 refers to probe; 510 refers to first driver; 520 refers to second driver; and 530 refers to detector;
600 refers to bladder; 700 refers to measured position; and 800 refers to target sectional image; and
900 refers to visual reference identifier; 910 refers to central point; 920 refers to pointing identifier group; 921 refers to first identifier; and 922 refers to second identifier.

DETAILED DESCRIPTION

The embodiments of the present disclosure will be described in detail hereinafter. Examples of the embodiments are shown in the drawings. The same or similar reference numerals throughout the drawings denote the same or similar elements or elements having the same or similar functions. The embodiments described below by reference to the drawings are exemplary and are intended only to explain the present disclosure and are not to be construed as limiting the present disclosure.

In the description of the present disclosure, it should be understood that the orientation or positional relationship indicated by the terms upper, lower, inner and outer is based on the orientation or positional relationship shown in the drawings, only for the convenience of describing the present disclosure and simplifying the description, and does not indicate or imply that the indicated device or element must have a specific orientation, or be constructed and operated in a specific orientation. Therefore, the terms should not be construed as limiting the present disclosure.

In the description of the present disclosure, if first and second are described, the descriptions are used for the purpose of distinguishing the technical features only, and cannot be understood as indicating or implying relative importance, or implicitly indicating the number of technical features indicated thereby, or implicitly indicating the order of technical features indicated thereby.

In the description of the present disclosure, unless otherwise explicitly defined, words such as setting, mounting and connecting should be understood in a broad sense, and those skilled in the art can reasonably determine the specific meanings of the above words in the present disclosure in combination with the specific contents of the technical solutions.

The existing bladder volume measuring method often relies on a user to control a position and an angle of a detector through use experience and subjective feeling of the user to position a bladder of the subject. However, it is difficult to position the bladder directly and successfully only by the user to subjectively place a probe. Therefore, it is necessary to move the probe after placing to position the bladder. However, the user cannot determine the next target moving direction of the probe, but can only move the probe randomly, which leads to a long time required for positioning and reduces the measurement efficiency.

Figure 1:
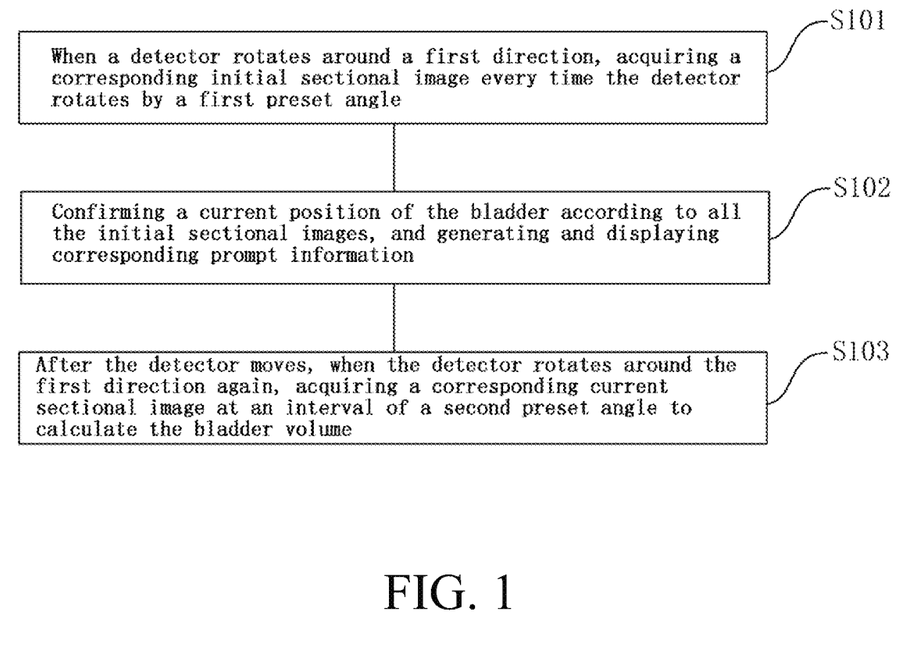
FIG. 1 is a flowchart of a bladder volume measuring method according to an embodiment of the present disclosure.

Therefore, some embodiments of the present disclosure provide a bladder volume measuring method, which is specifically shown in FIG. 1.

Figure 5:
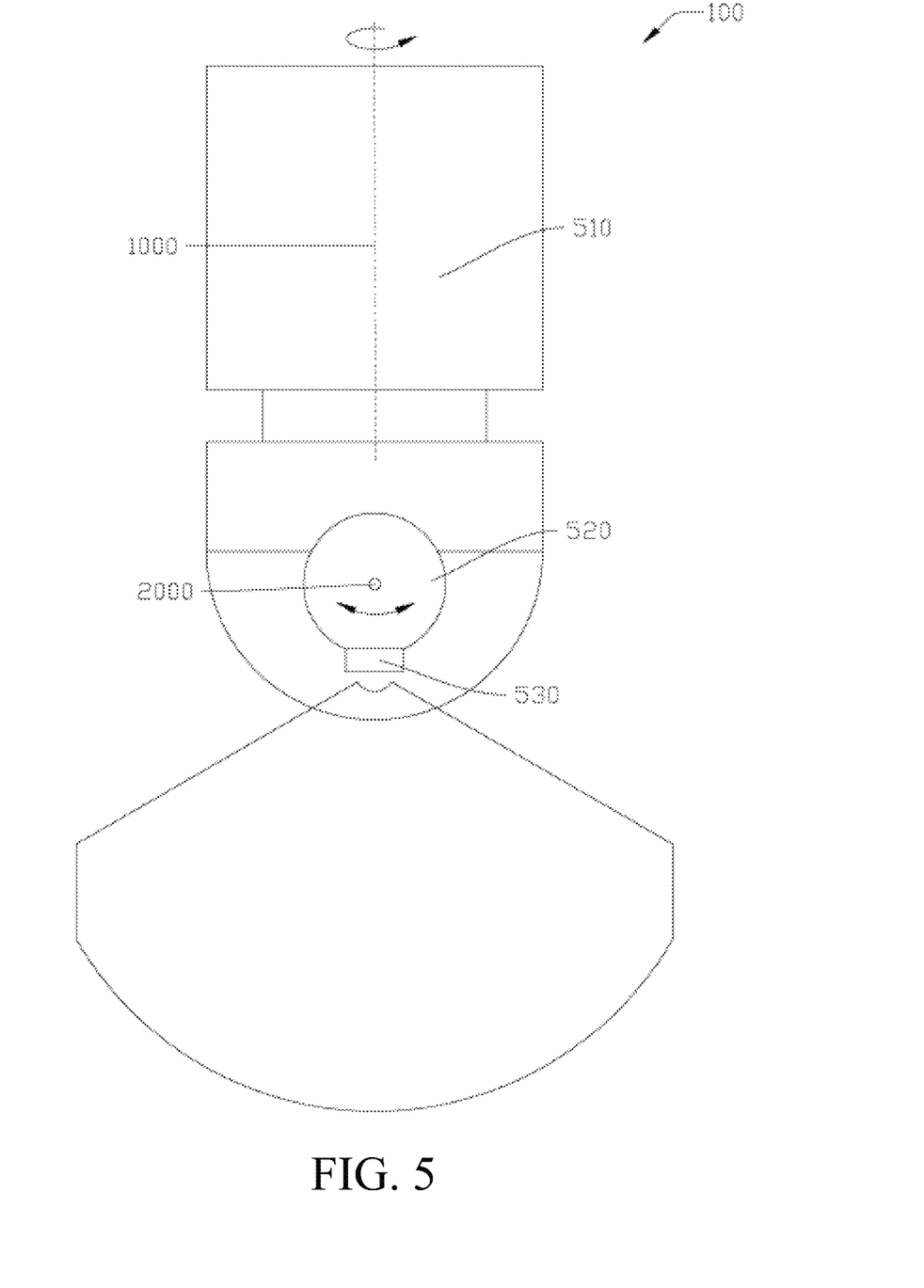
FIG. 5 is a schematic diagram of a probe of a test device in a bladder volume measuring method according to an embodiment of the present disclosure.
Figure 6:
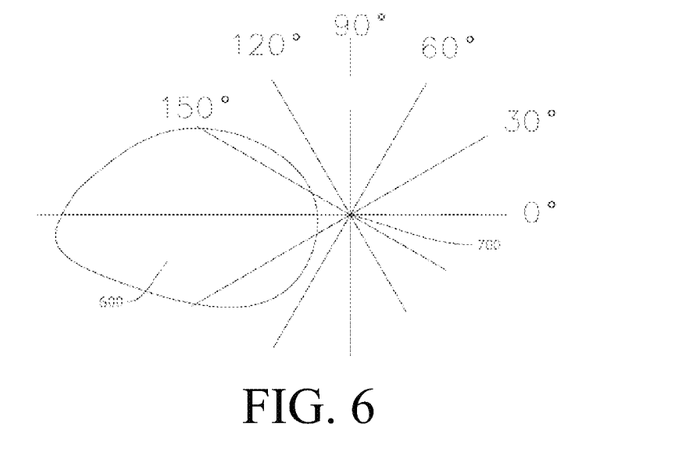
FIG. 6 is a schematic diagram of a probe located in an initial position in a bladder volume measuring method according to an embodiment of the present disclosure.
Figure 7:
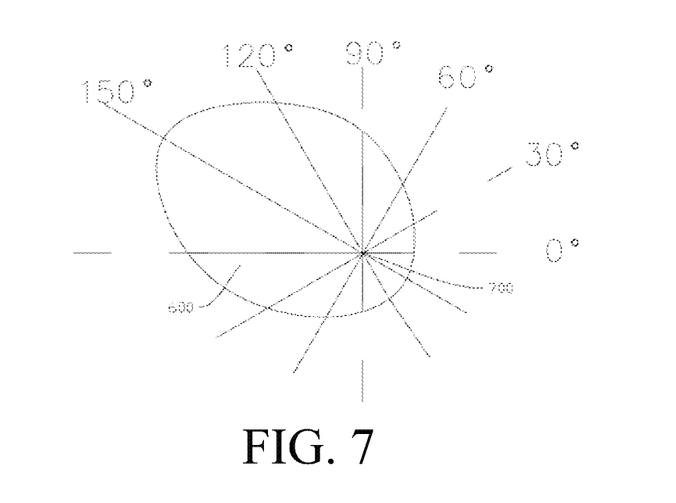
FIG. 7 is a schematic diagram after the probe moves in the bladder volume measuring method according to an embodiment of the present disclosure.

In the embodiments of the present disclosure, the bladder volume measuring method may be applied to a measuring device. It can be understood that, in this embodiment, the measuring device may be an ultrasonic measuring instrument, and the measuring device may comprise a probe 500 and a detector 530 for acquiring a sectional image of a bladder 600. Referring to FIG. 5, FIG. 6 and FIG. 7, the detector 530 may be arranged inside the probe 500, and the probe 500 may be used for being held by a user. The detector 530 can rotate around a first direction 1000, so as to realize 360-degree scanning of a measured position 700. Based on this, the first direction 1000 may be a direction of a connecting line between the detector 530 and the measured position 700.

As shown in FIG. 1, in the embodiments of the present disclosure, the measuring method may comprise the following steps.

At step S101, when the detector 530 rotates around the first direction 1000, a corresponding initial sectional image is acquired every time the detector rotates by a first preset angle.

In the embodiments of the present disclosure, the user may hold the probe 500 to detect and scan a subject, and in this case, the measured position 700 may be an initial position of the probe 500. It can be understood that it is difficult to successfully position the bladder 600 at one time only by subjectively placing the probe 500 by the user. Therefore, in this embodiment, the probe 530 can rotate around the first direction 1000. In the process of rotation, the corresponding initial sectional image can be acquired every time the detector rotates by the first preset angle, and the initial sectional image may be used as a basis for positioning the bladder 600. It should be noted that the first preset angle may be 30 degrees or 15 degrees, and may also be set by those skilled in the art according to the actual situation, which is not limited in this embodiment.

Referring to FIG. 5, in the embodiments of the present disclosure, the measuring device may also comprise a controller, a first driver 510 for driving the detector 530 to rotate around the first direction 1000, and a second driver 520 for driving the detector 530 to swing around a second direction 2000, wherein the second direction 2000 may be parallel to the measured position 700. The controller may be connected with the first driver 510 and the second driver 520 to send an instruction signal, and the instruction signal comprises a first instruction and a second instruction. It can be understood that the first driver 510 can drive the detector 530 to rotate around the first direction 1000, so as to realize 360-degree scanning. The second driver 520 can drive the detector 530 to swing around the second direction 2000, thus acquiring the initial sectional images. In this embodiment, the initial sectional images may be sector images obtained by ultrasonic imaging.

In the embodiments of the present disclosure, the measuring method may be applied to the controller, and the step S101 may comprise:
  a first operation S1011: sending the first instruction to the first driver 510; the first instruction being used for triggering the first driver 510 to drive the detector 530 to rotate around the first direction 1000 by the first preset angle; and a second operation S1012: sending the second instruction to the second driver 520 to acquire the corresponding initial sectional image; the second instruction being used for triggering the second driver 520 to drive the detector 530 to swing around the second direction 2000.

It can be understood that in the embodiments of the present disclosure, after receiving the first instruction, the first driver 510 can drive the detector 530 to rotate around the first direction 1000 by the first preset angle, for example, the first driver 510 drives the detector 530 to rotate from 0 degree to 30 degrees. After the detector 530 completes rotation, the second driver 520 can receive the second instruction, and then the second driver 520 drives the detector 530 to swing around the second direction 2000, so as to acquire the corresponding initial sectional image corresponding to the current angle. For example, when the detector 530 rotates to 30 degrees, the acquired initial sectional image corresponds to 30 degrees. In this embodiment, the controller can repeat the first operation and the second operation until the detector 530 rotates for one circle, that is, the 360-degree scanning is completed and the acquisition of all the initial sectional images is completed.

At step S102, a current position of the bladder 600 is acquired according to all the initial sectional images, and corresponding prompt information is generated and displayed; the prompt information being used for prompting a user to move the detector 530.

In the embodiments of the present disclosure, the current position of the bladder 600 can be confirmed by analyzing and comparing all the initial sectional images, and the current position of the bladder 600 can be accurately determined after the user places the detector 530. It can be understood that on the basis of confirming the current position of the bladder 600 and the initial position of the probe 500, the next target moving direction of the probe 530 can be known. In this embodiment, the corresponding prompt information can be generated and displayed according to the target moving direction, so as to prompt the user to move the probe 500 to the current position of the bladder 600 according to the prompt information, thus realizing the positioning of the bladder 600 by the probe 500, improving the positioning accuracy of the bladder 600, greatly shortening the time required for positioning the bladder 600 and improving the positioning efficiency of the bladder 600.

At step S103, after the detector 530 moves, when the detector 530 rotates around the first direction 1000 again, a corresponding current sectional image is acquired at a second preset angle to calculate the bladder volume.

In the embodiments of the present disclosure, after the user moves the probe 500 to the current position of the bladder 600 according to the prompt information, the probe 530 can rotate around the first direction 1000 again, and the corresponding current sectional images can be acquired at the second preset angle during the rotation, so as to obtain all the current sectional images. According to all the current sectional images, corresponding data of the bladder 600 can be acquired, so as to calculate the bladder volume. In this embodiment, the second preset angle may be the same as or different from the first preset angle. It should be noted that the second preset angle may be 30 degrees or 15 degrees, and may also be set by those skilled in the art according to the actual situation, which is not limited in this embodiment.

The measuring device disclosed in the embodiments of the present disclosure comprises the detector 530 for acquiring the sectional image of the bladder 600, the detector 530 can rotate around the first direction 1000, and the first direction 1000 is the direction of the connecting line between the detector 530 and the measured position 700. The measuring method comprises the steps of, when the detector 530 rotates around the first direction 1000, acquiring the corresponding initial sectional image every time the detector rotates by the first preset angle; confirming the current position of the bladder 600 according to all the initial sectional images, and generating and displaying the corresponding prompt information; the prompt information being used for prompting the user to move the detector 530; and after the detector 530 moves, when the detector 530 rotates around the first direction 1000 again, acquiring the corresponding current sectional image at the second preset angle to calculate the bladder volume. The present disclosure realizes that the user can accurately determine the current position of the bladder 600 after placing the detector 530, and can send the prompt information to the user according to the current position of the bladder 600, so as to prompt the user about the next target moving direction of the detector 530, reduce the dependence on the use experience and subjective feeling of the user, improve the positioning accuracy of the bladder 600, greatly shorten the time required for positioning the bladder 600, improve the positioning efficiency of the bladder 600, further improve the bladder volume measurement accuracy and greatly improve the measurement efficiency at the same time. In addition, the full interaction between the measuring device and the user can also improve the use experience of the user.

Some embodiments of the present disclosure provide another bladder volume measuring method. Referring to FIG. 5, in the embodiments of the present disclosure, the bladder volume measuring method may be applied to a measuring device. The measuring device may comprise a detector 530 for acquiring a sectional image of the bladder 600, the detector 530 can rotate around a first direction 1000, and the first direction 1000 is a direction of a connecting line between the detector 530 and a measured position 700.

Figure 2:
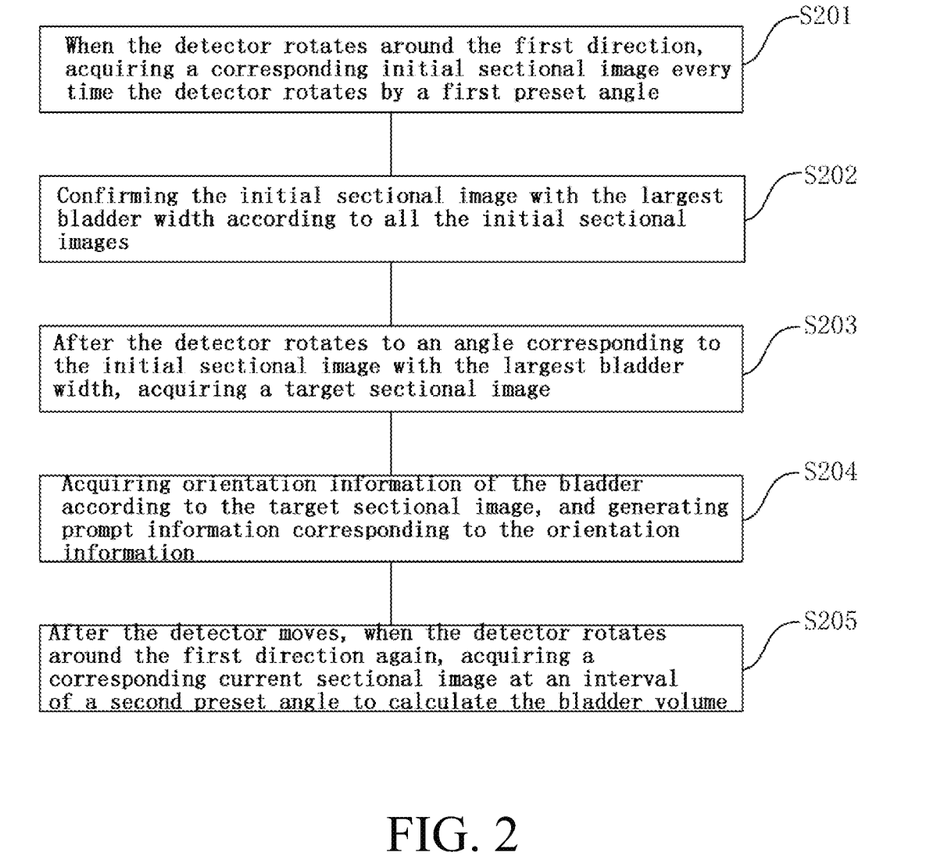
FIG. 2 is a flowchart of another bladder volume measuring method according to an embodiment of the present disclosure.

As shown in FIG. 2, in the embodiments of the present disclosure, the measuring method may comprise the following steps.

At step S201, when the detector 530 rotates around the first direction 1000, a corresponding initial sectional image is acquired every time the detector rotates by a first preset angle.

It should be noted that, regarding the particular implementation of the embodiments of the present disclosure, reference may be made to the related description in the foregoing embodiments. To avoid repetition, details are not described herein again.

At step S202, the initial sectional image with the largest bladder 600 width is confirmed according to all the initial sectional images.

At step S203, after the detector 530 rotates to an angle corresponding to the initial sectional image with the largest bladder 600 width, a target sectional image 800 is acquired.

Referring to FIG. 6 and FIG. 7, in the embodiments of the present disclosure, the initial sectional image with the largest bladder 600 width can be confirmed by comparing the largest bladder 600 width in all the initial sectional images. Specifically, the initial sectional image with the largest bladder 600 width in all the initial sectional images may be calibrated as the target sectional image 800. For example, the initial sectional image corresponding to the initial sectional image with the largest bladder 600 width of 0 degree in FIG. 6 may be calibrated as the target sectional image 800. In this embodiment, the first driver 510 can drive the detector 530 to rotate to an angle corresponding to the initial sectional image with the largest bladder 600 width. For example, as shown in FIG. 6, the initial sectional image with the largest bladder 600 width is 0 degree, the first driver 510 can drive the detector 530 to rotate to 0 degree, and then the second driver 520 can drive the detector 530 to swing to obtain the target sectional image 800 corresponding to 0 degree.

At step S204, orientation information of the bladder 600 is acquired according to the target sectional image 800, and prompt information corresponding to the orientation information is generated.

In the embodiments of the present disclosure, the current position of the bladder 600 can be confirmed by analyzing and comparing the target sectional image 800, and the current position of the bladder 600 can be accurately determined after the user places the detector 530. On the basis of confirming the current position of the bladder 600 and the initial position of the probe 500, the orientation information of the bladder 600 can be known, so as to know the next target moving direction of the detector 530. Therefore, this embodiment can generate and display the corresponding prompt information according to the orientation information, so as to prompt the user to move the probe 500 to the current position of the bladder 600 according to the prompt information.

At step S205, after the detector 530 moves, when the detector 530 rotates around the first direction 1000 again, a corresponding current sectional image is acquired at a second preset angle to calculate the bladder volume.

In the embodiment of the disclosure, the step S205 may comprise:

step S2051: acquiring all current edge data corresponding to all the current sectional images one by one according to all the current sectional images; and step S2052: calculating the bladder volume according to all the current edge data.

Referring to FIG. 7, in the embodiments of the present disclosure, after the detector 530 moves, the detector 530 may rotate around the first direction 1000 again, and the corresponding current sectional image can be acquired at the second preset angle during the rotation so as to acquire all the current sectional images. In the embodiment, the corresponding current edge data can be acquired from the current sectional image, so that the detector 530 may rotate around the first direction 1000 again, and the corresponding current sectional image can be acquired at the second preset angle during the rotation so as to acquire all the current sectional images. In this embodiment, the bladder volume may be calculated through all the current edge data, and those skilled in the art may select a calculating method according to the actual situation, which is not limited in this embodiment.

Some embodiments of the present disclosure provide another bladder volume measuring method. Referring to FIG. 5, in the embodiments of the present disclosure, the bladder volume measuring method may be applied to a measuring device. The measuring device may comprise a detector 530 for acquiring a sectional image of the bladder 600, the detector 530 can rotate around a first direction 1000, the first direction 1000 is a direction of a connecting line between the detector 530 and a measured position 700, and orientation information comprises a target moving direction.

Figure 3:
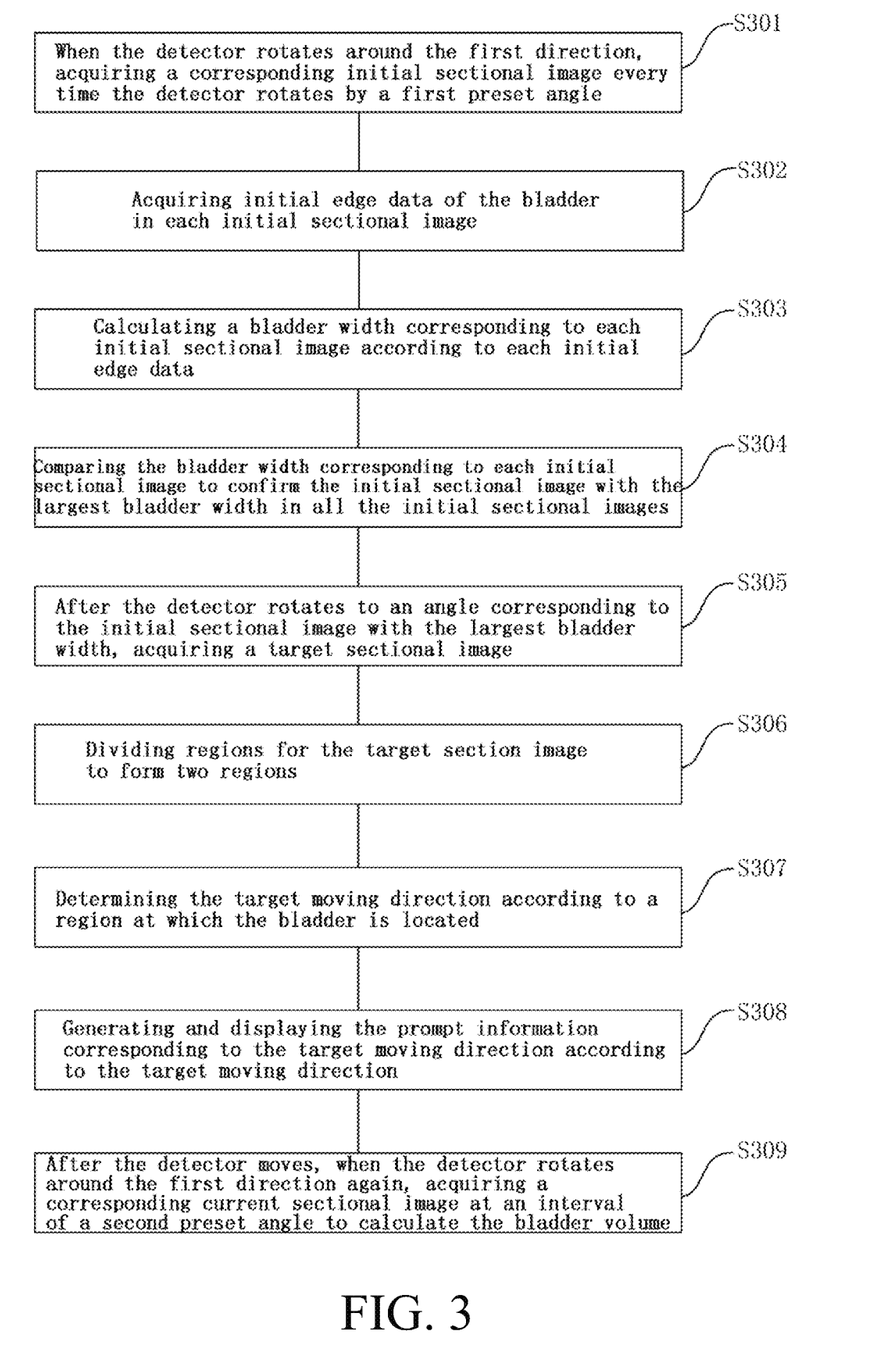
FIG. 3 is a flowchart of another bladder volume measuring method according to an embodiment of the present disclosure.

As shown in FIG. 3, in the embodiments of the present disclosure, the measuring method may comprise the following steps.

At step S301, when the detector 530 rotates around the first direction 1000, a corresponding initial sectional image is acquired every time the detector rotates by a first preset angle.

It should be noted that, regarding the particular implementation of the embodiments of the present disclosure, reference may be made to the related description in the foregoing embodiments. To avoid repetition, details are not described herein again.

At step S302, initial edge data of the bladder 600 in each initial sectional image is acquired.

At step S303, a bladder 600 width corresponding to each initial sectional image is calculated according to each initial edge data.

In the embodiments of the present disclosure, the initial sectional image may have the initial edge data of the bladder 600, and based on this, the bladder 600 width can be calculated according to the actual edge data in this embodiment. It can be understood that in this embodiment, the initial edge data may be coordinate data. For example, this embodiment can acquire the coordinate data of two opposite ends in the initial sectional image, so as to calculate the bladder 600 width. This embodiment can acquire the initial edge data of the bladder 600 in each initial sectional image, so as to calculate the bladder 600 width corresponding to each initial sectional image.

At step S304, the bladder 600 width corresponding to each initial sectional image is compared to confirm the initial sectional image with the largest bladder 600 width in all the initial sectional images.

In the embodiments of the present disclosure, each initial sectional image may have a corresponding bladder 600 width, and the initial sectional image with the largest bladder 600 width in all the initial sectional images can be confirmed by comparing the bladder 600 width corresponding to each initial sectional image.

At step S305, after the detector 530 rotates to an angle corresponding to the initial sectional image with the largest bladder 600 width, a target sectional image 800 is acquired.

It should be noted that, regarding the particular implementation of the embodiments of the present disclosure, reference may be made to the related description in the foregoing embodiments. To avoid repetition, details are not described herein again.

At step S306, regions are divided for the target section image 800 to form two regions.

At step S307, the target moving direction is determined according to a region at which the bladder 600 is located.

Figure 8:
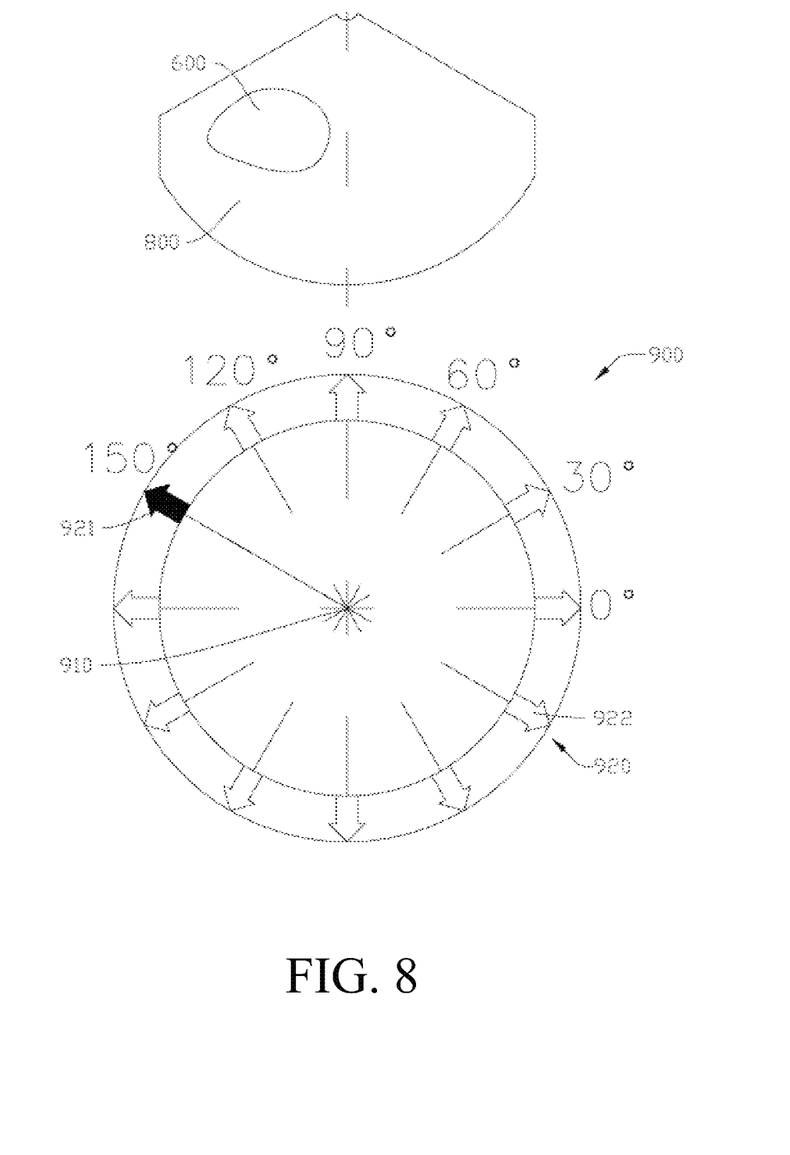
FIG. 8 is a schematic diagram of a visual reference identifier in a bladder volume measuring method according to an embodiment of the present disclosure.
Figure 9:
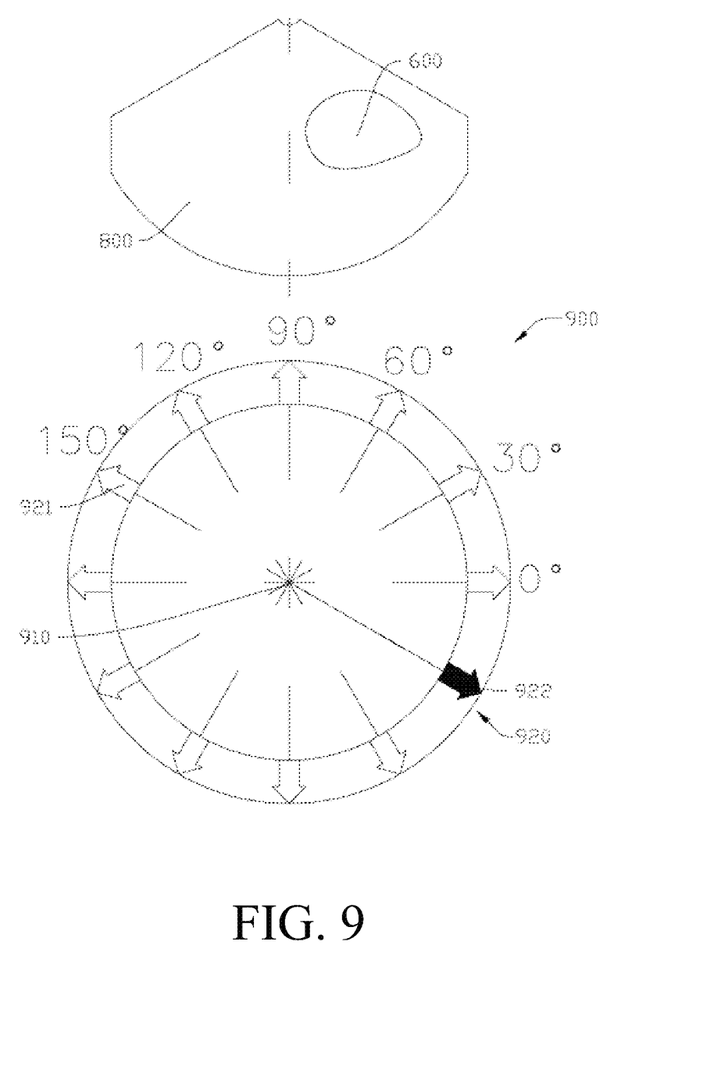
FIG. 9 is a schematic diagram of a visual reference identifier in another bladder volume measuring method according to an embodiment of the present disclosure.
Figure 10:
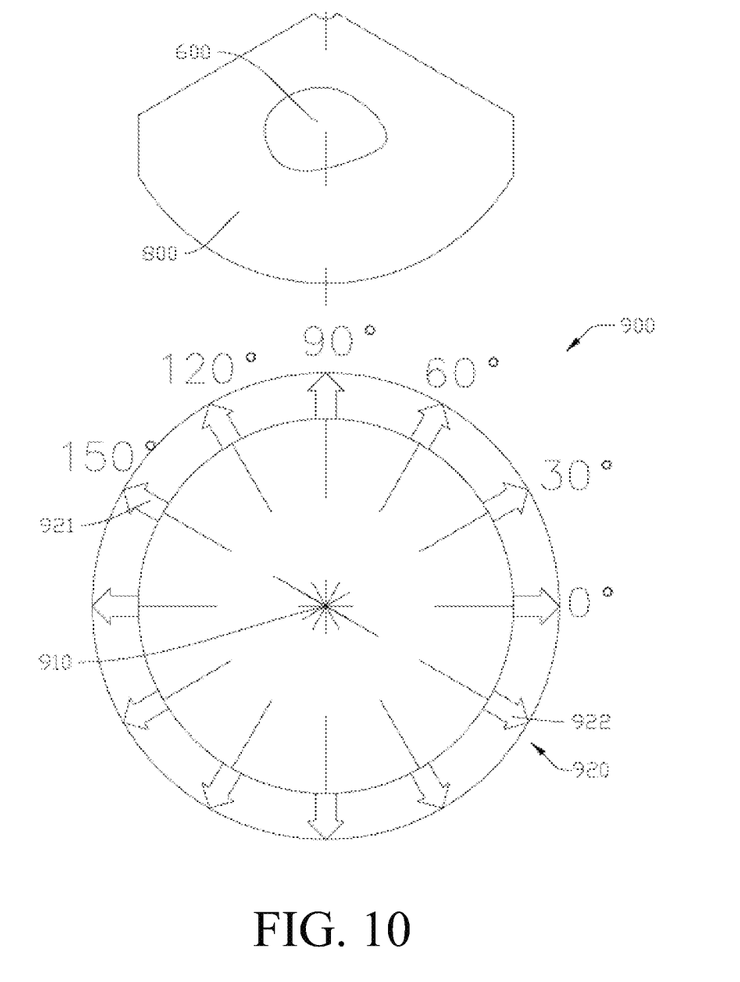
FIG. 10 is a schematic diagram of a visual reference identifier in another bladder volume measuring method according to an embodiment of the present disclosure.

Referring to FIG. 8, FIG. 9 and FIG. 10, in the embodiments of the present disclosure, a display device can display the target sectional image 800 and divide the target sectional image 800 into two regions by a dividing line, for example, the dividing line may be located in a center of the target sectional image 800 and divide the target sectional image into a left region and a right region. This embodiment can determine the target moving direction by determining the region where the bladder 600 is located. For example, referring to FIG. 8, an angle corresponding to the target sectional image 800 is 150 degrees, and on this basis, the bladder 600 is located in the left region of the target sectional image 800, then the target moving direction is to move to the left along the direction of 150 degrees. For example, referring to FIG. 9, an angle corresponding to the target sectional image 800 is 150 degrees, and on this basis, the bladder 600 is located in the right region of the target sectional image 800, then the target moving direction is to move to the right along the direction of 150 degrees. Referring to FIG. 10, an angle corresponding to the target sectional image 800 is 150 degrees, and on this basis, one part of the bladder 600 is located in the left region of the target sectional image 800, and the other part is located in the right region of the target sectional image 800, which means that the initial position of the probe 500 coincides with the bladder 600, and it is unnecessary to move the probe 500.

At step S308, the prompt information corresponding to the target moving direction is generated and displayed according to the target moving direction.

It should be noted that, regarding the particular implementation of the embodiments of the present disclosure, reference may be made to the related description in the foregoing embodiments. To avoid repetition, details are not described herein again.

Referring to FIG. 8, FIG. 9 and FIG. 10, in the embodiments of the present disclosure, the prompt information may comprise a visual reference identifier. The measuring device further comprises a display device for displaying the visual reference identifier. The display device may also display the target sectional image 800. In this embodiment, the visual reference identifier may form a visual prompt for the user to move the probe 500. Specifically, the step S308 may comprise the following steps.

At step S3081, the visual reference identifier is generated and displayed.

Referring to FIG. 8, FIG. 9 and FIG. 10, in the embodiments of the present disclosure, the visual reference identifier may comprise a central point 910 and a plurality of pointing identifier groups 920, wherein the central point 910 may correspond to a dividing line, and the plurality of pointing identifier groups 920 are arranged around the central point 910 at an interval of the first preset angle. Each pointing identifier group 920 comprises a first identifier 921 and a second identifier 922 pointed to opposite directions, and the first identifier 921 and the second identifier 922 correspond to the two regions one by one to represent the target moving direction. For example, the first identifier 921 and the second identifier 922 are located on an extension line extending along 150 degrees and point to opposite directions. Based on this, the first identifier 921 located to a left side of the center point 910 may correspond to the left region in the target sectional image 800, whereas the first identifier 921 located to a right side of the center point 910 may correspond to the right region in the target sectional image 800.

At step S30982, the pointing identifier group 920 corresponding to the angle corresponding to the target sectional image 800 is calibrated as a target identifier group.

At step S30983, the first identifier 921 or the second identifier 922 in the target identifier group is highlighted.

In the embodiments of the present disclosure, when the angle corresponding to the target sectional image 800 is 150 degrees, the target identifier group is the pointing identifier group 920 located on the extension line extending along 150 degrees. Referring to FIG. 8, when the bladder 600 is located in the left region in the target sectional image 800, the first identifier 921 can be highlighted. Referring to FIG. 9, when the bladder 600 is located in the right region in the target sectional image 800, the second identifier 922 can be highlighted, thus prompting the user about the target moving direction. It should be noted that in this embodiment, the highlighting may be highlighted display, color change display, shape change display, and the like. Those skilled in the art can choose the setting according to the actual situation, and this embodiment is not limited to this.

At step S309, after the detector 530 moves, when the detector 530 rotates around the first direction 1000 again, a corresponding current sectional image is acquired at a second preset angle to calculate the bladder volume.

It should be noted that, regarding the particular implementation of the embodiments of the present disclosure, reference may be made to the related description in the foregoing embodiments. To avoid repetition, details are not described herein again.

Figure 4:
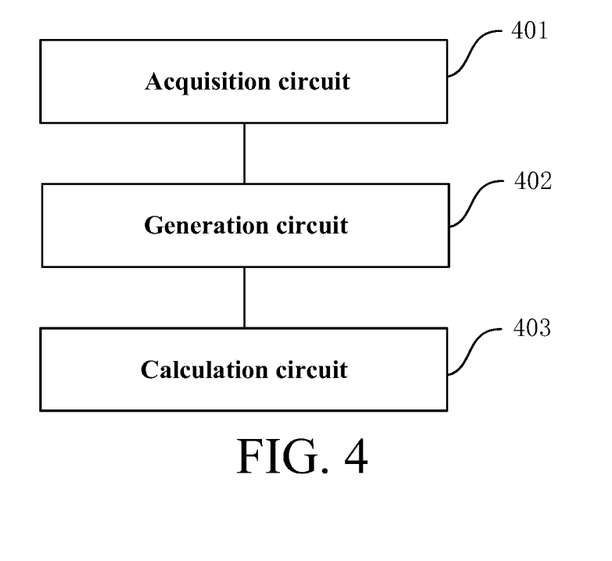
FIG. 4 is a schematic structural diagram of a bladder volume measuring system according to an embodiment of the present disclosure.

Some embodiments of the present disclosure provide a bladder volume measuring system 400, which is specifically shown in FIG. 4.

Referring to FIG. 5, in the embodiments of the present disclosure, the volume measuring system 400 is applied to a measuring device, the measuring device comprises a detector 530 for acquiring a sectional image of a bladder 600, the detector 530 is capable of rotating around a first direction 1000, and the first direction 1000 is a direction of a connecting line between the detector 530 and a measured position 700.

As shown in FIG. 4, the measuring system 400 may comprise:

an acquisition circuit 410 configured for, when the detector 530 rotates around the first direction 1000, acquiring a corresponding initial sectional image every time the detector rotates by a first preset angle;

a generation circuit 420 configured for confirming a current position of the bladder 600 according to all the initial sectional images, and generating and displaying corresponding prompt information; the prompt information being used for prompting a user to move the detector 530; and a calculation circuit 430 configured for, after the detector 530 moves, when the detector 530 rotates around the first direction 1000 again, acquiring a corresponding current sectional image at an interval of a second preset angle to calculate the bladder volume.

As the bladder volume measuring system 400 adopts all the technical solutions of the bladder volume measuring method of the above embodiments, the bladder volume measuring system has at least all the beneficial effects brought by the technical solutions of the above embodiments, and will not be described here again.

Some embodiments of the present disclosure provide an electronic device, comprising: a processor, a memory and a computer program stored in the memory and executable on the processor, wherein the computer program, when executed by the processor, implements each process of the bladder volume measuring method above, and can achieve the same technical effects. To avoid repetition, further description is omitted here.

Some embodiments of the present disclosure provide a computer readable storage medium, wherein: the computer readable storage medium stores a computer program thereon, and the computer program, when executed by a processor, implements each process of one embodiment of the bladder volume measuring method above, and can achieve the same technical effects. To avoid repetition, further description is omitted here.

The various embodiments in this specification are described in a progressive manner. Each embodiment focuses on the differences from the other embodiments, and the same or similar parts between the various embodiments may be referred to each other.

It should be appreciated by those skilled in the art that the embodiments of the present disclosure may be provided as methods, apparatuses or computer program products.

Accordingly, the embodiments of the present disclosure can take the form of an entirely hardware embodiment, an entirely software embodiment, or a combination embodiment of software and hardware. Moreover, the embodiments of the present disclosure may take the form of a computer program product embodied on one or more computer usable storage media (including but not limited to disk storage, CD-ROM, optical storage, etc.) in which computer usable program codes are included.

The embodiments of the present disclosure are described with reference to the flow charts and/or block diagrams of the method, terminal device (system), and computer program products according to the embodiments of the present disclosure. It should be appreciated that each flow and/or block in the flow charts and/or block diagrams, and combinations of the flows and/or blocks in the flow charts and/or block diagrams may be implemented by computer program instructions. These computer program instructions may be provided to a general purpose computer, a special purpose computer, an embedded processor, or a processor of other programmable data processing terminal device to produce a machine for the instructions executed by the computer or the processor of other programmable data processing terminal device to generate a device for implementing the functions specified in one or more flows of the flow chart and/or in one or more blocks of the block diagram.

The computer program instructions may also be provided to a computer readable memory that can guide the computer or other programmable data processing terminal device to work in a given manner, so that the instructions stored in the computer readable memory generate a product including a computer program instruction apparatus that implements the functions specified in one or more flows of the flow chart and/or in one or more blocks of the block diagram.

These computer program instructions may also be loaded to a computer, or other programmable terminal device, so that a series of operating steps are executed on the computer, or other programmable terminal device to produce processing implemented by the computer, so that the instructions executed in the computer or other programmable terminal device provide steps for implementing the functions specified in one or more flows of the flow chart and/or in one or more blocks of the block diagram.

Although the preferred embodiments of the present disclosure have been described, those skilled in the art can make additional changes and modifications to these embodiments once they know the basic inventive concepts. Therefore, the appended claims are intended to be interpreted as including the preferred embodiments and all the changes and modifications that fall within the scope of the embodiments of the present disclosure.

Finally, it should also be noted that relational terms herein such as first and second, etc., are used merely to distinguish one entity or operation from another entity or operation, and do not necessarily require or imply there is any such relationship or order between these entities or operations. Moreover, the terms "including", "comprising" or any variations thereof are intended to embrace a non-exclusive inclusion, such that a process, a method, an article, or a terminal device including a series of elements, includes not only those elements but also includes other elements not expressly listed, or also includes elements inherent to such process, method, article, or terminal device. In the absence of further limitation, an element defined by the phrase "including a . . . " does not exclude the presence of additional identical element in the process, method, article, or terminal device.

The embodiments of the present disclosure are described in detail with reference to the above drawings. Finally, it should be noted that the above embodiments are only used to illustrate the technical solutions of the present disclosure, but not to limit the technical solutions. Although the present disclosure has been described in detail with reference to the foregoing embodiments, those of ordinary skills in the art should understand that: the technical solutions described in the foregoing embodiments can be still modified, or some or all of the technical features can be equivalently replaced. However, these modifications or substitutions do not make the essence of the corresponding technical solutions depart from the scope of the technical solutions of various embodiments of the present disclosure.

The invention claimed is:

1. A bladder volume measuring method, applied to a measuring device and the measuring method comprises:
    when a detector of the measuring device rotates around a first direction, acquiring a corresponding initial sectional image of the bladder every time the detector rotates by a first preset angle; wherein the first direction is a direction of a connecting line between the detector and a measured position;
    confirming a current position of the bladder according to all the initial sectional images, and generating and displaying corresponding prompt information; the prompt information being used for prompting a user to move the detector; and
    after the detector moves, when the detector rotates around the first direction again, acquiring a corresponding current sectional image at an interval of a second preset angle to calculate the bladder volume;
    wherein the confirming a current position of the bladder according to all the initial sectional images, and generating and displaying corresponding prompt information comprises:
        confirming the initial sectional image with the largest bladder width according to all the initial sectional images;
        after the detector rotates to an angle corresponding to the initial sectional image with the largest bladder width, acquiring a target sectional image; and
        acquiring orientation information of the bladder according to the target sectional image, and generating prompt information corresponding to the orientation information;
    wherein the orientation information comprises a target moving direction, and the acquiring orientation information of the bladder according to the target sectional image, and generating prompt information corresponding to the orientation information comprises:
        dividing regions for the target section image to form two regions;
        determining the target moving direction according to a region at which the bladder is located; and
        generating and displaying the prompt information corresponding to the target moving direction according to the target moving direction;
    wherein the prompt information comprises a visual reference identifier, and the measuring device further comprises a display device for displaying the visual reference identifier, and the generating and displaying the prompt information corresponding to the target moving direction according to the target moving direction comprises:

generating and displaying the visual reference identifier; the visual reference identifier comprising a central point and a plurality of pointing identifier groups, the plurality of pointing identifier groups being arranged around the central point at an interval of the first preset angle, and each pointing identifier group comprises a first identifier and a second identifier pointing to opposite directions, and the first identifier and the second identifier corresponding to the two regions one by one to represent the target moving direction;

calibrating the pointing identifier group corresponding to the angle corresponding to the target sectional image as a target identifier group; and highlighting the first identifier or the second identifier in the target identifier group.

2. The bladder volume measuring method according to claim 1, wherein the confirming the initial sectional image with the largest bladder width according to all the initial sectional images comprises:

acquiring initial edge data of the bladder in each initial sectional image;

calculating a bladder width corresponding to each initial sectional image according to each initial edge data; and comparing the bladder width corresponding to each initial sectional image to confirm the initial sectional image with the largest bladder width in all the initial sectional images.

3. The bladder volume measuring method according to claim 1, wherein the acquiring a corresponding current sectional image at an interval of a second preset angle to calculate the bladder volume comprises:

acquiring all current edge data corresponding to all the current sectional images one by one according to all the current sectional images; and calculating the bladder volume according to all the current edge data.

4. An electronic device, comprising: a processor, a memory, and a computer program stored on the memory and operable on the processor, wherein the computer program, when executed by the processor, implements the bladder volume measuring method according to claim 1.

5. A non-transitory computer readable storage medium, wherein the computer readable storage medium stores a computer program thereon, and the computer program, when executed by a processor, implements the bladder volume measuring method according to claim 1.

* * * * *